(12) United States Patent
Gamez-Garcia

(10) Patent No.: US 7,381,417 B2
(45) Date of Patent: Jun. 3, 2008

(54) FRAGRANCE DELIVERY SYSTEM FOR SURFACE CLEANERS AND CONDITIONERS

(75) Inventor: Manuel Gamez-Garcia, Flemington, NJ (US)

(73) Assignee: Firmenich SA, Geneva (CH)

( * ) Notice: Subject to any disclaimer, the term of this patent is extended or adjusted under 35 U.S.C. 154(b) by 32 days.

(21) Appl. No.: 11/408,179

(22) Filed: Apr. 21, 2006

(65) Prior Publication Data

US 2006/0210508 A1 Sep. 21, 2006

Related U.S. Application Data

(63) Continuation of application No. PCT/IB2004/003544, filed on Oct. 28, 2004.
(60) Provisional application No. 60/516,548, filed on Oct. 31, 2003.

(30) Foreign Application Priority Data

Oct. 31, 2003 (WO) .................. PCT/IB03/04867

(51) Int. Cl.
*A61K 9/00* (2006.01)
(52) U.S. Cl. .................................... 424/401
(58) Field of Classification Search ............... 424/70.1, 424/70.11, 401
See application file for complete search history.

(56) References Cited

U.S. PATENT DOCUMENTS 5,804,538 A 9/1998 Wei et al. ................... 510/101

(Continued)

FOREIGN PATENT DOCUMENTS

EP 1 146 057 A1 10/2001

(Continued)

OTHER PUBLICATIONS

S. Escher et al., "A Quantitative Study of the Factors That Influence the Substantivity of Fragrance Chemicals on Laundered and Dried Fabrics," JAOCS, vol. 71, No. 1, Jan. 1994, pp. 31-40.

(Continued)

*Primary Examiner*—Shelley A. Dodson
*Assistant Examiner*—Konata M George
(74) *Attorney, Agent, or Firm*—Winston & Strawn LLP

(57) ABSTRACT

We claim a fragrance delivery system consisting of a mixture of various polymers oligomers and stabilizers capable of forming a surfactant complex gel dispersion when combined with a cleansing surfactant base and yielding high levels of fragrance deposition onto the skin, hair or other surface such as a textile, from a cleansing or softening consumer product comprising a micelle forming surfactant. The internal phase or dispersible phase of this surfactant complex gel dispersion (GLPPD) is made of a mixture of various immiscible polymers, oligomers and stabilizers forming a complex gel with the surfactant platform and whose ratio and composition are selected to dissolve preferentially a wide range of fragrance raw materials. The selection criteria are, first, that the fragrance should present a higher fragrance partitioning ratio into the surfactant complex gel phase than into the free micelles of the surfactant, second, that the surfactant complex gel should not be further solubilized by the free micelles, and third, that the polymer mixture selected should complex with the surfactant system. The external or dispersing phase of the GLPPD is made of a single cationic polymer or a mixture of cationic polymers that have been hydrated and associated with the surfactant to form a complex gel structure that cannot be further solubilized by the free micelles.

36 Claims, 5 Drawing Sheets

U.S. PATENT DOCUMENTS

| | | |
|---|---|---|
| 5,843,875 A | 12/1998 | Wei et al. .................. 510/101 |
| 5,869,070 A | 2/1999 | Dixon et al. ................ 424/401 |
| 5,891,833 A | 4/1999 | Wei et al. .................. 510/121 |
| 6,200,937 B1 * | 3/2001 | Brennan et al. ............ 510/119 |
| 6,312,678 B1 | 11/2001 | Elliott et al. ............. 424/70.22 |
| 6,491,902 B2 | 12/2002 | Shefer et al. ............. 424/70.1 |
| 2001/0053753 A1 | 12/2001 | Engekhart .................. 510/130 |
| 2002/0035406 A1 | 3/2002 | Lukenbach et al. ......... 510/122 |
| 2002/0055452 A1 | 5/2002 | McGee et al. ................ 512/2 |
| 2003/0139502 A1 | 7/2003 | Ricca ........................ 524/156 |
| 2003/0202952 A1 * | 10/2003 | Wells et al. ............. 424/70.13 |
| 2004/0087476 A1 | 5/2004 | Dykstra et al. ................ 512/2 |
| 2004/0091445 A1 | 5/2004 | Dykstra et al. .......... 424/70.17 |

FOREIGN PATENT DOCUMENTS

| | | |
|---|---|---|
| EP | 1 216 685 A2 | 6/2002 |
| WO | WO 99/43777 | 9/1999 |

OTHER PUBLICATIONS

P. Müller et al., "What Makes a Fragrance Substantive," Perfumer & Flavorist, vol. 18, Jul./Aug. 1993, pp. 45-49.

* cited by examiner

FRAGRANCE DELIVERY SYSTEM FOR SURFACE CLEANERS AND CONDITIONERS

CROSS REFERENCE TO RELATED APPLICATIONS

This application is a continuation of Application No. PCT/IB2004/003544 filed Oct. 28, 2004, which claims the benefit of U.S. Application No. 60/516,548 filed Oct. 31, 2003. The entire content of each prior application is expressly incorporated herein by reference thereto.

BACKGROUND OF THE INVENTION

The present invention relates to a fragrance carrier and delivery system formed of mixtures of water miscible and immiscible polymers or oligomers able to form a surfactant complex gel dispersion capable of yielding high levels of fragrance deposition onto the skin, hair or other surfaces such as tiles or textiles, from a cleansing consumer product comprising a mixture of surfactants. The internal and external phases, or dispersible and dispersing phases, of this surfactant complex gel dispersion are formed when a mixture of various polymers, oligomers and optionally stabilizers are combined with a surfactant cleansing system to form an association surfactant complex structure with a polymer to polymer ratio, (polymer/oligomer/stabilizer mixture) to surfactant ratio, and composition that are selected so as to dissolve fragrance raw materials having a wide range of solubilities and volatilities.

Fragrance enhanced deposition and long lastingness are two benefits commonly searched for when formulating body or hair washes, liquid soaps, detergents and softeners, intended to be applied on the skin, hair, textile or other surfaces, all these products containing cleansing or conditioning surfactants or surface active agents. The amount of fragrance deposition on said surfaces, and its longlastingness, are however limited because most fragrances are solubilized in the free surfactant micelles and washed off by the cleansing or conditioning surfactant system present in these types of consumer products.

Fragrances are typically oily substances that, when added to a surfactant-containing composition, become solubilized in the surfactant micelles by partitioning. This process limits the amount of fragrance deposition on the surface treated with the composition, firstly, because the fragrance is greatly diluted in the micelles, and, secondly, because the small amount of fragrance that is deposited upon micelle breakage is re-solubilized back into the surfactant system.

Attempts to solve this problem have led to the use of cationic polymers, alone or in combination with fragrance carriers, in the surfactant solution. Fragrance deposition by these systems onto the surface, in particular the skin, is mainly attained by the use of either a cationic surfactant or a cationic polymer. Typical prior art in this field is represented for example by U.S. Pat. Nos. 5,804,538, 5,843,875 and 5,891,833. These documents all describe the use of cationic polymers to assist in enhanced fragrance deposition from body washes onto the skin.

Fragrance carriers used in the prior art typically consist of either a cationic polymer alone, that forms ion pairs with the surfactant, or a cationic polymer combined with oily liquid droplets in which the fragrance is dissolved, or combined with hydrophobic solid waxes or polymeric solid particles in which the fragrance is encapsulated.

The main drawbacks of using a cationic polymer forming ion pairs with a surfactant is that the level of fragrance binding is extremely low and therefore these carrier systems do not show a high level of fragrance deposition on the treated surface.

Drawbacks presented by carrier systems that resort to the use of cationic polymers in combination with oily liquid droplets are, first, that the oil in itself is partially solubilized in the surfactant micelles, and second, that the fragrances gradually diffuse out of the oil droplets by partitioning into the micelles when the cleansing composition reaches thermodynamic equilibrium. These two processes reduce significantly the level of fragrance deposition onto the surface on which the product is applied. A typical example of this type of solution is the fragrance delivery system described in US patent application 2002/0055452.

Hydrophobic waxes and polymeric solid particles, although not solubilized by the surfactant micelles because of their solid character, still lose fragrance by partitioning into the micelles. Furthermore, solid particles are difficult to deposit onto the skin, hair and other surfaces, since they do not break during shear, and in addition they are easily removed during washing.

U.S. Pat. No. 6,491,902 and European patent application 1 146 057 are pertinent examples of prior art describing the use of solid polymeric particles as fragrance carriers.

Encapsulation of fragrances in hollow spheres, nanosomes, liposomes, microspheres, etc., present similar challenges. In most cases, the solid walls of these spheres are unstable at high surfactant concentrations and they are also permeable, allowing the gradual partitioning of fragrances into the surfactant micelles.

In summary, the main problems posed by these prior known techniques are: first, that they lose fragrance into the surfactant micelles by partitioning, second, that, when the hydrophobic vehicle is a triglyceride or mineral oil, it can be solubilized into the micelles, and third, that when the vehicle is a solid particle, or has solid walls, it cannot be broken by shear, thus preventing fragrance deposition, and that it also allows the gradual diffusion of fragrances into the micelles.

In more recent documents such as US 2004/0087476 and 2004/0091445, there is described the use of cationic polymeric particles which are preferably not admixed with the fragrance prior to addition thereof to the end product containing the surfactant. The cationic polymers in question must have affinity to specific perfumery raw materials having defined characteristics. In addition, the fragrance polymeric systems there-described must obey certain parameters which are not generally defined or current in the art, but are defined only in the above-mentioned documents. In other words, the described resulting fragrance carriers or polymeric fragrance particles are quite specific and relate only to specific cationic polymers and fragrance raw materials, as mentioned in the examples. The drawback of this type of system is the danger that the skilled perfumer may be limited in his activity and choice of perfumery materials by having to formulate fragrances mainly as a function of the carrier polymer available, rather than on the basis of his hedonic objectives.

In fact, in the art of perfumery and more particularly of fragrance delivery and deposition on substrates treated with perfumed, surfactant-containing, consumer products, it is highly desirable to be able to deal with fragrance carrier systems that are as universal as possible, i.e. that can be easily adapted to the general characteristics of the end consumer product with which the surface or substrate is treated, without overly restricting the palette of materials that the perfumer has at his disposal for creating pleasant, original and effective fragrances meeting consumer preferences. The present invention addresses precisely this problem and also obviates the other problems encountered in the prior art of reference.

We have now surprisingly been able to establish that a more general solution to the prior art problems abovementioned is that of providing a fragrance carrier system that takes into account the composition of the end product base, in particular the nature of the essential component in skin, hair, textile and other surface cleaners and conditioners, i.e. the surface active agent or surfactant system.

The present invention thus provides a fragrance carrier and delivery system which essentially consists of a gel complex resulting from the interaction of the fragrance carrier/deposition polymer combination with the surfactant molecules contained in the end product. The fragrance carrier/deposition combination comprises various types of water miscible and immiscible polymers, oligomers, and optionally stabilizers, able to form association complexes with the surfactant molecules at any dilution, when combined with the cleansing/conditioning surfactant platform.

We have now been able to establish that surfactant complex gel structures produced by combination of carefully selected mixtures of water miscible and immiscible polymers and/or oligomers optionally stabilized, with cleansing surfactant systems in particular, enable the formation of higly substantive gels which preferentially dissolve the fragrance and allow its effective deposition on the surfaces being cleansed. The external dispersing phase of such gel-liquid polymer/polymer dispersions (hereinafter referred to as "GLPPD"), which are one object of the invention, consists of a water miscible cationic polymer, or a mixture of water-miscible cationic polymers, able to form an aqueous surfactant complex gel when combined with a detergent surfactant system, whereas the internal dispersible phase of the GLPPD consists of one or more water immiscible liquid polymers or oligomers, and optionally stabilizers, also able to form complexes with a cleansing surfactant. The GLPPD can be made in situ in the surfactant base or be prepared separately and then added to the surfactant base. The fragrance, which can be of any appropriate composition, can also be admixed with the GLPPD, separately from the surfactant base, or be added after the complex gel has been formed in the surfactant base.

SUMMARY OF THE INVENTION

The present invention provides a carrier and delivery system for a hydrophobic benefit agent, namely a fragrance, comprising: a) a water miscible cationic polymer or mixture of cationic polymers susceptible of forming a complex gel with a surfactant system; b) one or more liquid water immiscible polymers or oligomers susceptible of complexing said surfactant system; and c) a hydrophobic benefit agent; said carrier and delivery system being capable of forming a gel-liquid polymer/polymer dispersion (GLPPD) with said surfactant system when admixed thereto, so as to provide a stable surfactant-polymer gel able to solubilize the hydrophobic agent and prevent its partitioning into free surfactant micelles.

By "free surfactant micelles" it is meant here the surfactant micellar mass generally present in a surfactant-containing consumer product composition, namely a surface cleanser or conditioner consumer product, and which consists of unbound surfactant, i.e. surfactant that is not complexed by the carrier delivery system according to the invention, when the latter is incorporated in said consumer product.

The present invention thus relates to a carrier/delivery system for fragrance or another hydrophobic benefit agent, able to form a surfactant complex gel structure more preferably a gel surfactant/polymer/polymer dispersion system obtainable by admixture of: a) a dispersing phase formed of one or more water miscible cationic polymers susceptible of complexing a cleansing surfactant system to form an aqueous gel; b) a dispersible phase which is formed of one or more water immiscible polymers and/or oligomers, and optionally stabilizers, susceptible of forming a complex with said surfactant system; and c) a hydrophobic benefit agent.

Following a specific embodiment of the invention, the hydrophobic benefit agent is a fragrance.

By "carrier and delivery" it is meant here the combination of the actions of carrying the fragrance through the washing or treatment of the surface, and the transfer and deposition onto said surface of the hydrophobic agent, namely the fragrance, contained in the cleansing or treating consumer product applied to said surface.

The dispersing polymer phase according to the invention is a water miscible cationic polymer or mixture of cationic polymers susceptible of complexing cleansing surfactants to form a gel. Preferred such cationic polymers include the polymer Acrylamidopropyltrimonium Chloride Acrylamide Copolymer commercialized by Ciba under the trade name SALCARE® SC-60, or mixtures thereof with POLYQUATERNIUM® 10 of Amerchol, commercialized under the tradename Polymer JR-400, Polymer JR-30M, Polymers LR-400 and LR-30M; Trimethylaminoethyl Methacrylate Chloride Polymer sold under the trade names SALCARE® SC-95 and SALCARE® SC-96 by Ciba; Polyethylenimine PS sold under the trade name LUPASOL® PS by BASF; Cationic Polyamine, supplied by Cytec under the trade name SUPERFLOC® C-583; Polyvinylamine commercialized under the trade name LUPAMIN® 9096 by BASF; Cationic Polyacrylamide commercialized under the trade name SUPERFLOC® C-498 from Cytec; and Polydimethyldiallyl Ammonium Chloride or PolyDADMAC, commercialized under various trade names.

The liquid dispersible phase is formed of one or more liquid water immiscible polymers or oligomers, and optionally stabilizers.

The water immiscible polymers or oligomers suitable for the invention include the isophorone di-isocyanate copolymer derivatives commercialised by Alzo under the tradenames of Polyderm® and Monoderm® (see Table further on in the text); polyisobutene/polybutene derivatives (see Table further on in the text); and hydrogenated polydecene and hydrogenated C6-C14 olefin polymers commercialised by ExxonMobil Chemical Co under the trade names PureSyn® 2, 4, 6, 8, 10, 40, 100, 150, 300, 1000, 3000.

Suitable stabilizers according to the invention include trihydroxystearin commercialised under trade names Thixcin® R or Rheocin®, by Elementis and Sud Chemie, respectively; Polysorbate 20, commercialised under various trade names, and sorbitan isostearate commercialized under the trade name Crill-6 by Croda.

The invention also relates to a process for manufacturing the carrier and delivery system which comprises: a) mixing the water immiscible dispersible polymer or polymers or oligomers and optionally stabilizers with the hydrophobic ingredient, namely a fragrance, to obtain the dispersible phase (Part A); b) hydrating the dispersing cationic polymer or mixture of cationic polymers in a water-containing medium so as to obtain a hydrophilic polymer solution (Part B); c) mixing Part A and B in appropriate relative proportions to form a polymer dispersion (Part C), and d) incorporating Part C into the surfactant system so as to obtain a surfactant/ polymer/fragrance gel complex delivery system according to the invention.

Another object of the invention is a consumer product comprising a. surfactant/polymer/fragrance gel according to the invention. Such consumer products include body washes and shampoos, liquid soaps and detergents for cleaning surfaces, such as dishwashers and heavy duty liquids, hard surface cleansers, textile and tile detergents and fabric softeners.

DETAILED DESCRIPTION OF THE PREFERRED EMBODIMENTS

Figure 1:
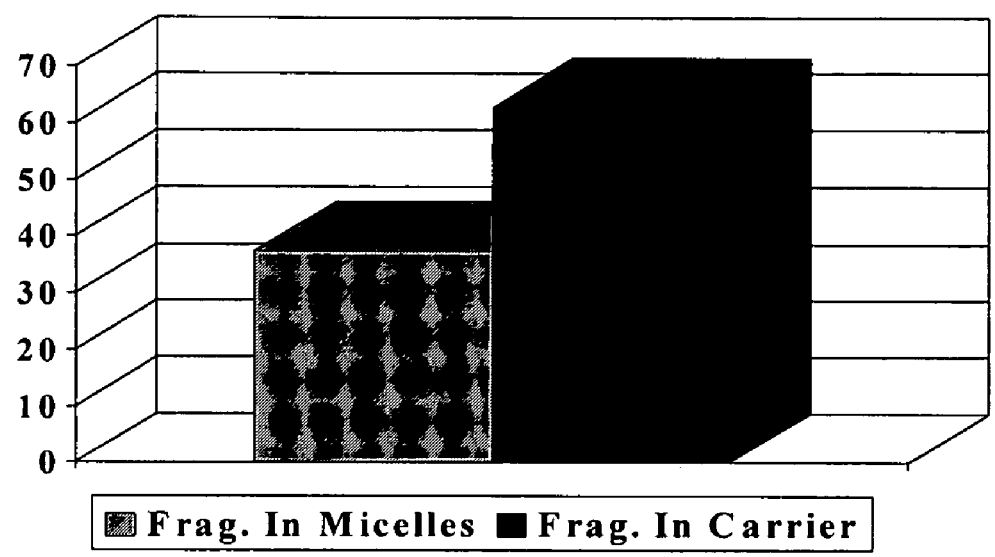
FIG. 1 shows the calculated percentages of fragrance found in the micellar solution and in the dispersed particles of body wash composition A according to the invention Example 1.

As indicated above, one of the objects of the invention is a carrier and delivery system for a hydrophobic benefit agent, in particular a fragrance, which delivery system is a gel surfactant complex formed when various water miscible and immiscible polymers, oligomers and stabilizers are combined with the surfactant molecules in the cleansing composition. The surfactant complex gel is suceptible of dissolving the fragrance preferentially and is obtained by admixing: a) a dispersing phase which is a cationic polymer or mixture of cationic polymers susceptible of forming a complex/surfactant gel phase when mixed with the cleansing surfactant and water; b) a dispersible phase which is a mixture of water immiscible polymers, oligomers and optionally stabilizers, also with the ability to form a complex with the cleansing surfactant; and c) a hydrophobic benefit agent.

This gel-liquid polymer/polymer dispersion (GLPPD) of the invention is characterised by the following features: A) the chemical composition and mix ratio of the polymers, oligomers and stabilizers used either alone or in combination, in the internal dispersible phase of the GLPPD is selected in a manner to ensure that the solubility of the fragrance is higher in the formed surfactant complex gel than in the remaining free surfactant micelles, i.e. the micelles of the surfactant not bound by the said complex and which are present in the end consumer product in which the fragrance delivery system of the invention is intended to be used; in this manner the surfactant complex gel droplets will retain high levels of fragrance even after thermodynamic equilibrium has been established between the surfactant complex gel droplets and the said free surfactant micelles not bound to the complex; B) the molecular weight, chemical composition and concentration of the liquid dispersible polymers, oligomers and stabilizers, forming the internal phase of the GLPPD, is chosen such that the polymer/oligomer chain mixture of the surfactant complex gel droplets cannot be solubilized in the free micelles of the end product surfactant not bound by the polymers; this prevents the surfactant complex gel containing the fragrance from being solubilized, diluted, and washed away by the free micelles; C) the final viscosity of the liquid surfactant complex gel droplets mixed with the fragrance is selected in a range between 500 and 20,000 cps, so as to allow said surfactant complex gel to form a stiff gel in the end-product surfactant solution; this range of viscosities also allows an easy deformation of the surfactant complex gel droplets with shear during application or foaming; in body care products, this advantageously allows for an even distribution of the product onto the keratin surface of the skin; D) the dispersing polymer forming the external phase of the gel is chosen to be a cationic polymer or a mixture of cationic polymers capable of complexing high levels of the cleansing surfactant, from 1% to 30% by weight of the total surfactant amount in the end product, or preferably from 3% to 25% thereof. This dispersing complex, when combined with the internal dispersible phase described above, will produce a highly cationic and hydrophobic surfactant complex gel, with high affinity for the surface of application, in particular when transferred onto said surface from the colloidal phase formed during the application of the consumer end-product, and more specifically, from the foam thereof in the case of shampoos or body washes; the cationic polymer or mixture of cationic polymers shall thus be selected so as to have a degree of cationic substitution within the range of 3 to 30 meq/g, more preferably between 5 to 25 meq/g, and a molecular weight higher than 400 K; and E) the surfactant complex gel containing the fragrance is homogeneously dispersed in the end product composition, and forms gel droplets or particles with a diameter ranging from 0.01 to 10 microns. The particles are susceptible of stabilization with the above described stabilizers, and thus remain stable and are resistant to the foaming shear and the dilution process during washing.

Following these features of the invention, the person skilled in the art will be able to select, without undue effort, the appropriate cationic gel-forming dispersing polymers and the dispersible polymers, oligomers and stabilizers, as a function of the fragrance composition and the surfactant-containing end product in which the fragrance is used. In the presence of aqueous surfactant solutions, the surfactant complex gel dispersion of the invention, carrying the benefit hydrophobic ingredient, such as a fragrance, shall break into small droplets/particles during the application process, the latter being capable of retaining and transferring the fragrance from the lamellar phase of the foam, or from any other colloidal phase formed during the product application, onto the surface being washed, in a far more effective manner than prior known fragrance carrier systems. The fragrance delivery onto the surface of use, skin, hair, textile, window glass or tiles, for example, shall be far more efficient, as illustrated by the examples presented further on.

The cationic polymer or mixture of polymers used as the dispersing phase of the GLPPD are appropriately selected from the group consisting of: POLYQUATERNIUM® 10 (quaternized hydroxyethylcellulose); origin: Amerchol Corporation; UCARE® Polymer JR-125; JR-400; JR-30M; LR-400; LR-30M; origin: Amerchol Corporation; POLYQUATERNIUM®-7 (copolymer of diallyl dimethyl ammonium chloride and acrylamide); MERQUAT® 550, origin: Nalco Company; SALCARE® SC 10; origin: Ciba Speciality Chemicals; quaternized guar gum; JAGUAR® C-13S; origin: Rhodia, Meyhall Chemicals Ltd; JAGUAR® C-16S; origin: Rhodia, Meyhall Chemicals Ltd; Excel 2000; origin: Rhodia; acrylamidopropyltrimonium chloride (and)

acrylamide copolymer, SALCARE® SC-60; origin: Ciba Speciality Chemicals; polymethacrylamidopropyl triamomnium chloride, POLYCARE® 133; origin: Rhodia; polyethylenimine, LUPASOL® PS; origin: BASF; imidazol copolymer, LUVIQUAT® MS 370; origin: BASE; Cationic Polyamine, SUPERFLOC® C-583; origin Cytec; Cationic Polyacrylamide, SUPERFLOC® C-498; origin Cytec; Trimethylaminoethyl Methacrylate Chloride, SALCARE® SC-95 and SALCARE® SC-96; origin: Allied Colloids, Ciba, Polyvinylamine, LUPAMIN® 9096; origin BASF, and Polydimethyldiallyl ammonium Chloride, Poly DADMAC, under various trade names.

Two main types of chemical ingredients can be used according to the present invention, either alone or mixed, as the main constituents of the liquid internal dispersible phase of the GLPPD. One type is selected from a wide range of water immiscible polymers and oligomers, while the other, optional, type includes various types of emulsion stabilizers. The said water-immiscible polymers and oligomers can be derivatives of polyurethane or isophorone di-isocyanate; hydrogenated polyisobutene/polybutene copolymers; polydecene and hydrogenated polydecene; and hydrogenated C6-C14 olefin polymers. Mixtures of the above can also be used.

The polymers/copolymers of polyurethane are derived from isophorone di-isocyanate, a monomer containing various functional groups with different degrees of polarity and hydrophobic character. These polyurethane polymers are liquid or solid in nature and are capable of dissolving a wide range of fragrance raw materials.

The polymers/copolymers derived from hydrogenated polyisobutene/polybutene, on the other hand, are derived from the hydrophobic monomer isobutene/butene, whereas the polydecene polymers are synthesized from linear alfa polyolefines derived from the oligomerization of ethylene. These polymers are non-polar viscous liquids and can be used alone or in combination with the isophorone di-isocyante polymer derivatives to improve fragrance solubility. Preferably, mixtures of these two types of polymers will be used.

Suitable stabilizers include trihydroxystearin and sorbitan isostearate.

The following Table describes the water immiscible polymers, oligomers and stabilizers: these include polyurethane derivatives, hydrogenated polyisobutene/polybutene derivatives, hydrogenated polydecene derivatives, trihydroxystearin, Polysorbate 20 and sorbitan isostearate, all suitable to form the dispersible phase of the delivery system which is the object of the invention.

| Commercial Name | Chemical Description | Origin |
|---|---|---|
| POLYDERM ® PPI-BZ | Benzyl Alcohol-Ethylene Glycol/IPDI Copolymer | Alzo International Inc. |
| POLYDERM ® PPI-CA-15 | Di-PEG-15 Cocamine/IPDI Copolymer | Alzo International Inc. |
| POLYDERM ® PPI-CO | Castor Oil/IPDI Copolymer | Alzo International Inc. |
| POLYDERM ® PPI-CO-H | Hydrogenated Castor Oil/IPDI Copolymer | Alzo International Inc. |
| POLYDERM ® PPI-CO-40 | PEG-40 Hydrogenated Castor Oil/IPDI Copolymer | Alzo International Inc. |
| POLYDERM ® PPI-CO-200 | PEG-200 Hydrogenated Castor Oil/IPDI Copolymer | Alzo International Inc. |
| POLYDERM ® PPI-DGDIS | Diglycerol Diisostearate/IPDI Copolymer | Alzo International Inc. |
| POLYDERM ® PPI-GH | Glycereth-7 Hydroxystearate/IPDI Copolymer | Alzo International Inc. |
| POLYDERM ® PPI-PE | Diethylene Glycol Adipate/IPDI Copolymer | Alzo International Inc. |
| POLYDERM ® PPI-SA | Di-2 PEG Soyamine/IPDI Copolymer | Alzo International Inc. |
| POLYDERM ® PPI-SI | Dimethiconol/IPDI Copolymer | Alzo International Inc. |
| POLYDERM ® PPI-SI-50 | Dimethiconol/IPDI Copolymer 50% | Alzo International Inc. |
| POLYDERM ® PPI-SI/SA | Dimethiconol-PEG-2 Soyamine/IPDI Copolymer | Alzo International Inc. |
| POLYDERM ® PPI-SI-WI | Dimethicone Copolyol/IPDI Copolymer water insoluble | Alzo International Inc. |
| POLYDERM ® PPI-SI-WS | Dimethicone Copolyol/IPDI Copolymer water soluble | Alzo International Inc. |
| MONODERM ® MPI-BZ | Benzyl Alcohol Dimer/IPDI | Alzo International Inc. |
| MONODERM ® MPI-N-1-100 | PEG-100 Methyl Alcohol Dimer/IPDI | Alzo International Inc. |
| MONODERM ® MPI-12-3 | Laureth-3 Alcohol Dimer/IPDI | Alzo International Inc. |
| MONODERM ® MPI-1-14 | Isomyristyl Alcohol Dimer/IPDI | Alzo International Inc. |
| MONODERM ® MPI-1-16 | Isocetyl Alcohol Dimer/IPDI | Alzo International Inc. |
| MONODERM ® MPI-1-18 | Isostearyl Alcohol Dimer/IPDI | Alzo International Inc. |
| MONODERM ® MPI-N-18-100 | PEG-100 Stearyl Ether/Dimer/IPDI | Alzo International Inc. |
| MONODERM ® MPI-1-20 | Octyldodecyl Alcohol Dimer/IPDI | Alzo International Inc. |
| MONODERM ® MPI-1-24 | 2-Decyltetradecyl Alcohol Dimer/IPDI | Alzo International Inc. |
| MONODERM ® MPI-RC | Ricinoleamidopropyl Amine Dimer/IPDI | Alzo International Inc. |

-continued

| Commercial Name | Chemical Description | Origin |
| --- | --- | --- |
| AVALURE ® UR 450 Polymer | PPG-17/IPDI/DMPA Copolymer | Noveon |
| POLYSYNLANE ® Gel | Hydrogenated Polyisobutene (and) Butylene/Ethylene/Styrene Copolymer (and) Ethylene/Propylene/Styrene Copolymer | The Collaborative Group |
| POLYFIX ® JPN | Hydrogenated Polyisobutene (and) Polybutene | The Collaborative Group |
| POLYSYNLANE ® (HV) | Hydrogenated Polyisobutene | The Collaborative Group |
| SOPHIM ® MC-30 | | Sophim |
| SOPHIM ® MC-300 | | Sophim |
| Fancol Polysio 200, 250, 275, 300, 450, 800 | | The Fanning Corporation |
| PANALENE ® H300E | | Lipo Chemicals |
| PANALENE ® L-14E | | Lipo Chemicals |
| PURESYN ® 2, 4, 6, 8, 10, 40, 100, 150, 300, 1000, 3000 | Polydecene or Hydrogenated Polydecene | ExxonMobil Chemicals Co. |
| THIXCIN ® | | Triydroxystearin Elementis |
| Crill-6 | Sorbitan Isostearate | Croda |
| TWEEN ® 20 | Polisorbate 20 | Multiple suppliers |

As the hydrophobic benefit ingredient carried and deposited by way of the GLPPD there will be preferentially used a fragrance. The latter is a perfuming ingredient or mixture of ingredients, the choice of which is dictated by the hedonic effect that it is desired to achieve, as well as the type of product into which the fragrance will be incorporated. Typically, these are mixtures of chemical ingredients capable of imparting an odor to a substrate or surface such as skin, hair, textiles, a variety of surfaces such as dishes, tiles, windows, carpets, etc, and which are created by perfumers according to rules well established in the art of perfumery.

Generally speaking, by perfuming composition or fragrance, we mean here a composition comprising at least one perfuming ingredient and optionally one or more solvents or adjuvants commonly used in the perfume industry. It is understood that the perfuming ingredients are present in a perfuming effective amount.

By "perfuming ingredient" it is meant here a compound which is of current use in the perfumery industry, i.e. a compound which is used as active ingredient in a perfuming preparation or composition in order to impart a hedonic effect. In other words such an ingredient must be recognized by a person skilled in the art as being able to impart or modify in the desired manner the odor of a composition, and not just as having an odor.

The nature and type of the perfuming co-ingredients mentioned above do not warrant a more detailed description here, which in any case would not be exhaustive, the skilled person in the art being able to select them on the basis of its general knowledge and according to the nature of the product to be perfumed and the olfactory effect it is desired to achieve. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and said perfuming co-ingredients can be of natural or synthetic origin. Many of these ingredients are in any case listed in reference texts such as the book of S. Arctander, Perfume and Flavor Chemicals, 1969, Montclair, N.J., USA, or its more recent versions, or in other works of a similar nature, as well as in the abundant patent literature in the field of perfumery. As perfuming ingredients it is also possible to use compounds which are known to release in a controlled manner a perfumery compound.

Similarly, a detailed description of the nature and type of solvents commonly used in the perfume industry cannot be exhaustive. A skilled person in the art is able to select them on the basis of the nature of the product to be perfumed. However, as non-limiting examples of such solvents, one can cite, in addition to the solvents mentioned above, also ethanol, water/ethanol mixtures, limonene or other terpenes, isoparaffins such as those known under the trademark ISOPAR® (origin: Exxon Chemical) or glycol ethers and glycol ether esters such as those known under the trademark DOWANOL® (origin: Dow Chemical Company).

According to the invention, one of the main aims of the described delivery system is to increase the substantivity and long lastingness of the fragrance on the surface on which the latter is applied, and its composition will therefore be adapted to this aim, the perfumers being well acquainted with the principles regulating the choice of perfume ingredients to fulfil both the hedonic and the technical requirements of substantivity. The principles of achieving the latter have been widely described in the prior art and, in this context, pertinent examples thereof are the articles of Escher et al., "A Quantitative Study of Factors that Influence the Substantivity of Fragrance Chemicals on Laundered and Dried Fabrics", JOACS, vol. 71, no. 1 (1994) and that of Muller et al., "What makes a fragrance substantive", Perfumer and Flavorist, 1845-1849 (1993). Such well established principles have been repeated many times in more recent literature, namely in the patent literature, and even the non-specialist can now find many examples of suitable perfuming ingredients to be used according to the invention. To mention a single example in this context, such principles are again discussed at length for example on pages 1 and 2 of US 2002/0055452 previously mentioned, which document also cites older patent literature of pertinence in this field. Other prior art documents mentioned earlier in this text also cite many perfuming ingredients suitable for use in this invention. Notwithstanding such citations, it is to be noted here that none of such citations are to be considered as limiting the number and nature of perfuming ingredients suitable for use in the delivery system of the invention, in particular because, as previously mentioned, many known fragrance carrier systems described in these documents are mostly adapted to the delivery of specific, more restricted, fragrance compositions that what is the case in the present invention.

It should be made clear that the delivery system of the invention can be applied to any fragrance, the person skilled in the art being quite capable, without undue effort, by trial and error, to arrive at an optimum polymer/surfactant mixture capable of carrying and depositing the perfume which the perfumer created solely on the basis of the odor effect desired and the requirements dictated by the nature of the end product (stability of the fragrance in the base, both color and odorwise, the nature of other ingredients therein, the characteristics of substantivity, freshness, or other hedonic parameter requested by the end product manufacturer). The nature of the fragrance is therefore not an essential characteristic or parameter of the invention.

As cited earlier, the delivery system described above is prepared by a method which comprises: a) mixing the liquid dispersible polymer or polymers, oligomers and optionally stabilizers with the benefit hydrophobic ingredient, namely a fragrance, to obtain the dispersible phase; b) hydrating the cationic polymer or mixture of cationic polymers in a water-containing medium so as to obtain a hydrophilic polymer solution forming the dispersing phase; mixing first the dispersible and dispersing phases to form a pre-mix, and then combine the pre-mix in appropriate relative proportions with the surfactant base, so as to obtain a surfactant complex gel, the delivery system of the invention.

Said pre-mix is also an object of the present invention.

According to one embodiment of this process, the liquid polymer dispersible phase is prepared, as the case may be, by admixing the selected water miscible or immiscible polymers, when a mixture of polymers is desired, or by a mixture of polymers/oligomers, in proportions adapted to optimise the preferential dissolution of the fragrance in this phase and following the required features of this phase already disclosed previously. Once the liquid dispersible polymer mixture is optimised, it is admixed with the fragrance, the weight ratio of polymer/fragrance being comprised between 0.01:1 and 10:1.

The dispersing phase is then prepared by hydrating the cationic polymer or mixture of polymers in water, the ratio of cationic polymer to water varying between 1:40 and 1:80, to form the cationic solution.

The final step of the preparation of the GLPPD according to the invention comprises pre-mixing, under stirring, the cationic polymer solution and the dispersible phase, in a weight ratio comprised between 0.1:10 and 10:1 per weight, and then combining the pre-mixture of cationic polymers and water immiscible fragrance/polymers or fragrance/oligomers with the cleansing surfactant in a weight ratio comprised between 0.01/100 and 5/100, until a surfactant complex gel dispersion, having a particle size between 0.1 and 10 microns, is obtained. The optional emulsifying surfactants or stabilizers can be added either to the dispersible phase or later as the final step in the cleansing formulation. Such emulsifiers or stabilizers can be TWEEN™ 20 (origin: ICI/UNIQEMA), Crill 6 (origin: CRODA), THIXCIN® (origin: ELEMENTIS), and are added to improve the fragrance dissolving properties and for further stabilizing the surfactant complex gel dispersion.

The mixture of water miscible cationic polymers with water immiscible polymers or oligomers, optionally together with the stabilizers, is thus able to form a surfactant complex gel once added to the surfactant-containing end product, amongst those previously cited. The proportions in which this pre-mix of water miscible cationic polymer and water imiscible polymers or oligomers is added to the end product can vary in a wide range of values, for example in a weight ratio comprised between 0.1:10 and 10:1. In fact the concentration of GLPPD pre-mix added is selected so as to provide a typical fragrance concentration in the end product comprised between 0.001 and 10% by weight of the total weight of end product. More typical fragrance contents range from 0.4 or 0.5 to 1 or 2% of the end product weight.

Alternatively, the GLPPD of the invention can be directly prepared in situ in the surfactant-containing end product base, by adding, under vigorous stirring, the hydrated cationic polymer gel phase, obtained as described herein above, directly to said end product base, in a concentration adapted to reach a weight of cationic polymer gel comprised between 0.01 and 5% of the weight of surfactant base. The dispersible phase, comprising the mixture of water immiscible polymers, oligomers, and optionally stabilizers, and fragrance, is then added to the end product in a concentration sufficient to provide a total fragrance level of 0.001 to 10%, more preferably of 0.5 to 2% weight, relative to the total weight of the end product.

The fragrance delivery system of the invention can be used in a wide variety of end products typically containing micelle forming surfactants, to achieve better and more efficient fragrance deposition on the surfaces treated with such products. The invention also relates to a cleaning or treating product for the topical application on skin and hair, or for application on surfaces such as textiles, windows, dishes, tiles, plastic covers, etc, comprising a micelle forming surfactant and a benefit agent which is hydrophobic, particularly a fragrance. Specific examples of such end products include body washes and gels, shampoos and hair conditioners, liquid soaps and detergents, fabric softeners and heavy duty cleaners.

The composition and nature of the end product are immaterial for the object of the invention, the delivery system of the latter being adapted to be used in any such product, provided that the latter comprises a surfactant susceptible of forming micelles and a fragrance susceptible of partitioning into said micelles when the surfactant is not complexed by a misture of polymers according to the invention.

The prior art cited above in the present description provides many examples of such end products and the types of ingredients, other than the surfactant system and the fragrance, that they may optionally contain. Particular citation is made here of the extensive description of such products to be found for example in U.S. Pat. No. 5,804,538 or U.S. Pat. No. 5,843,875, the contents of which, inasmuch as they relate to the composition of the personal cleansing products there-described, are hereby included by reference. Other such pertinent descriptions of the general optional compositions of end products susceptible of being improved according to the present invention by addition of the fragrance delivery system described previously, and thus of being the object of this invention, can be found for example in International application WO 99/43777 the contents of which, inasmuch as they relate to current components of fabric softener end products, are also hereby included by reference.

It goes without saying that many other end product formulations, comprising micelle forming surfactants and fragrances, are included in the presently claimed end products. Surfactants capable of complexation with the GLPPD of the invention include any surfactant susceptible of forming micelles, and can be anionic, non-ionic, amphoteric, or cationic. Surfactants such as Ammonium Lauryl Sulfate, Ammonium Laureth Sulfate with 1, 2, or 3 moles of ethoxylation, Sodium Lauryl Sulfate, Sodium Laureth Sulfate with 1, 2, or 3 moles of ethoxylation, alone or combined with either Cocamido Propyl Betaine, Cocamide MEA or Disodium Cocoamphoacetate, Alkyl BenzeneSulfonate and Ethoxylated Lauryl Alcohols with 3 to 20 moles of ethoxylation, are particularly contemplated by the present invention and the products containing such surfactants are advantageously improved in their capability to deposit fragrance onto surfaces treated therewith. The performance of such products, related to the effectiveness of fragrance delivery to the surfaces treated therewith and to the longlastingness of the fragrance on said surfaces, can be vastly improved by the use of the fragrance delivery system according to the instant invention. The only selection criteria are, first, that the fragrance should present a higher fragrance partitioning concentration ratio into the surfactant complex gel formed by the GLPPD than into the free surfactant micelles not bound to the complex, and second, that the surfactant complex formed by the mixture of cationic polymers and water immiscible liquid polymers or oligomers, and optionally stabilizers, used according to the invention, is not solubilized by the free micelles not bound to surfactant complex gel.

Thus, in perfumery, one of the major advantages of the invention resides in the fact that the invention's delivery system imparts an intense fragrance to the treated surface, which would not be detected on said surface over the same period of time if prior art fragrance carrier systems had been employed.

Such a behavior makes the invention's delivery system particularly suitable as a precursor of perfuming ingredients for applications associated with functional or fine perfumery. Consequently, the use of an invention's delivery system as a perfuming ingredient, is another object of the present invention. In other words, a method to confer, enhance, improve or modify the odor properties of a perfuming composition or of a perfumed article, which method comprises adding to said composition or article an effective amount of the invention's delivery system, in any of its forms, is an object of the invention.

For the sake of clarity, it has to be mentioned that, by "consumer product base" or "end product" we mean here a consumer product, i.e. a consumable product such as a soap, a detergent or a perfume. In other words, a perfumed article according to the invention essentially comprises a functional formulation with a specific activity (cleaning or treating in any manner), as well as optional additional benefit agents, corresponding to a particular consumer product, and an odor effective amount of the invention's delivery system, in any of its forms.

The nature and type of the constituents of the consumer product base do not therefore warrant a more detailed description here, which in any case would not be exhaustive, the skilled person being able to select them on the basis of its general knowledge and as a function of the nature of the product and the perfuming effect that one desires to achieve.

The invention rests on the novel principle of using polymers, oligomers and stabilizers, either on their own or more preferably as mixtures, capable of forming association complex structures with cleansing or conditioning surfactant systems, thus yielding a surfactant complex gel dispersion for delivery of a benefit agent having an hydrophobic nature, namely for fragrance delivery, onto a surface or substrate. The dispersible fragrance carrier is either a mixture of polymers or oligomers derived from isophorone di-isocyanate, preferably viscous polymers or oligomers consisting of polyurethane or di-isocyanate derivatives, from hydrogenated polyisobutene/polybutene derivatives, or from hydrogenated polydecene, with trihydroxystearin, sorbitan isostearate or polysorbate 20, the viscosity of which is comprised between 100 and 20,000 cps. The dispersing/depositing phase is a mixture of high molecular weight cationic polymers able to disperse or dissolve in water, with a high degree of cationic substitution in its chains and the composition of which is attuned to that of the dispersible phase polymer mixture so as to minimize solubilization of the latter in the free micelles of the surfactant not bound to the surfactant complex, once the combination of fragrance carrier and depositing cationic polymer is incorporated into a surfactant containing product. Unlike prior known fragrance delivery systems, the fragrance carrier/delivery system of the invention, once complexed with the surfactant system, favors the partitioning and retention of the fragrance in the surfactant/polymer GLPPD, after thermodynamic equilibration with the non complexed or free micelles of the surfactant system in the end product, and is also more stable at high surfactant concentrations, wherein the abbreviations have the usual meaning in the art.

EXAMPLES

The invention will be described hereafter in a more detailed fashion by way of the examples described hereafter.

Example 1

Preparation of a Body Wash Composition According to the Invention

Two body wash compositions were prepared by admixing, as described below, the following ingredients in the proportions indicated:

1) Fragrance # 1: 1.0 g of a fragrance composition containing the following raw materials:

Limonene (15.5%); Benzyl Acetate (6.25%); Cyclohexanol Acetate (2.5%); Cyclohexanol, 2-(1,1-dimethylethyl)-, acetate (6.25%); 2-methyl Undecanal (2.75%); 4-(1,1-dimethylethyl)-alpha methyl benzenepropanal, (18.75%); Cyclopentaneacetic acid, 3-oxo-2-pentyl-, methylester (29.25%); Hexyl Salicylate (18.75%).

2) Polymers for internal dispersible phase (fragrance carrier component): 1.0 g of Isomyristyl Alcohol Dimer/IPDI (MONODERM® MPI-1-14) or 1.0 g of Hydrogenated Castor Oil/IPDI Copolymer 3) Polymer for external dispersing phase (fragrance deposit/delivery component): 0.5 g of Acrylamidopropyltrimonium Chloride (and) Acrylamide copolymer (SALCARE® SC-60)

4) Primary Surfactant 1: 15.0 g of Sodium Laureth-2 Sulfate

5) Secondary Surfactants: 3.0 g of Cocamido Propyl Betaine

6) Tertiary Surfactant: 2.0 g of Ethylene Glycol Distearate

7) Water: 75.4 g Water
8) Preservative: 0.1 g DMDM Hydantoin

Part A: The fragrance was admixed with the liquid dispersible carrier (respectively the first or the second cited polymer) referred to as fragrance carrier component, internal phase, using a simple mixer system. The mixture yielded a viscous transparent liquid with a viscosity of 6000 cps. Part B: The cationic dispersing polymer, referred to as fragrance depositing/delivery component, was hydrated by gradually mixing 0.5 g of polymer in 20 g of water until a clear solution was obtained. Part C: The primary, secondary, and tertiary surfactants were mixed and heated to 70 C. The remaining water was added as needed.

Part A was admixed with the same amount of part B and the mixture thoroughly stirred until a pre-mix dispersion was formed. The pre-mix was then added to part C at 40 C to form the surfactant/polymer gel complex or GLPPD, object of the invention, while cooling and stirring thoroughly until room temperature was reached. Two body wash products according to the invention were thus obtained.

Comparative Example 1

Preparation of a Comparative Body Wash Composition According to the Prior Art

A comparative body wash composition was prepared by admixing, as described below, the following ingredients in the proportions indicated:
1) Fragrance: 1.0 g the fragrance described in Example 1
2) Fragrance carrier component: Fatty ester oil: 3.0 g of Myristyl Myristate
3) Fragrance delivery component: 0.5 g of Acrylamidopropyltrimonium Chloride (and) Acrylamide copolymer (SALCARE® SC-60)
4) Primary Surfactant 1: 15.0 g of Sodium Laureth-2 Sulfate
5) Secondary Surfactants: 3.0 g of Cocamido Propyl Betaine
6) Tertiary Surfactant: 2.0 g of Ethylene Glycol Distearate
7) Water: 75.4 g Water
8) Preservative: 0.1 g DMDM Hydantoin Part A: The fragrance was admixed with the fragrance carrier, internal phase, using a simple mixer system. Part B: The cationic dispersing polymer, referred to as fragrance delivery component, was hydrated by gradually mixing 0.5 g of polymer in 20 g of water until a gel was obtained. Part C: The primary, secondary, and tertiary surfactants were mixed and heated to 70 C.

The remaining water was added as needed.

Part A was admixed with part B and the mixture thoroughly stirred until a gel/emulsion was obtained.

The mixture thus obtained was then added to part C at 40 C while cooling and stirring thoroughly until room temperature was reached. A comparative body wash product was thus obtained.

Example 2

Application of the Body Washes Described in Example 1 and Comparative Example 1, and Measurement of the Fragrance Release from the Surfaces Treated Fragrance deposition analyses from the body washes previously described in Example 1 (Composition A) were carried out on wool swatches. The wool swatches were 2½ wide by 4 inches long (1 gram) and were washed once with 0.5 g of the body wash formulation in question. The wool swatches were soaked in 500 ml of water before washing and the wash formula was applied on their surface. The wash was then gently stroked, rubbed and foamed on the wool swatch for about 30 seconds, after which the latter was rinsed in running tap water at 30 C. Fragrance analyses on the wool swatches were carried out by SPME (Solid Phase Micro Extraction) methods.

Wool swatches prepared for SPME analysis were put into vials after various periods of time had elapsed since the washing process. The SPME analysis of fragrance left on the wool after each period of time was carried out in the vial headspace by triplicate analysis.

Wool swatches were also washed in the same manner using the comparative body wash formulation obtained in Comparative Example (Composition B), containing the fatty ester myristyl myristate as the oily fragrance carrier.

The effects of the type of fragrance carrier on fragrance partitioning after thermodynamic equilibration had occurred in the body wash composition were assessed with the following procedure. Body wash composition A according to the invention and comparative body wash composition B were both allowed to age at 45 C for 15 days. After this period of time, both formulations were centrifuged and the dispersible particles of each formulation were separated from their liquid micellar phase. One gram of each phase was then put into vials and the headspace was analyzed by SPME. Previously, calibration curves had been made for each phase by spiking them with known amounts of fragrance.

FIG. 1 shows the calculated percentages of fragrance found in the micellar solution and in the dispersed particles of body wash composition A according to the invention. For the sake of simplicity the values in this graph represent fragrance percentages calculated on one fragrance raw material, namely, the raw material with the strongest signal in the chromatographic detector. The results in FIG. 1 indicate that after aging and thermodynamic equilibrium has been reached, the total amount of fragrance contained in the GLPPD system of the invention is higher than in the micellar solution.

Figure 2:
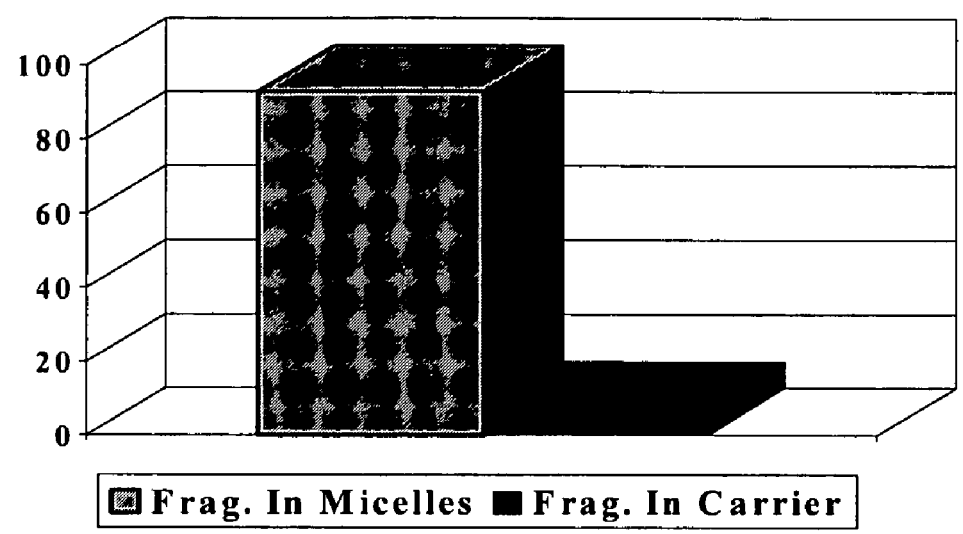
FIG. 2 shows the percentage of fragrance found in the surfactant micellar solution of comparative body wash composition B according to Comparative Example 2.

In contrast, the percentage of fragrance found in the micellar solution of comparative body wash composition B turned out to be higher than in the separated fatty ester used as an oily carrier, as shown in FIG. 2. It is important to note here that the fatty ester myristyl myristate was added at 3% to the comparative wash, and that, in the absence of ethylene glycol distearate, its appearance was slightly opaque. Also, it was observed that if myristyl myristate was added at 1% together with the fragrance at 1%, the mixture fragrance/fatty ester becomes totally solubilized by the surfactant micelles. These observations indicate that in the case of comparative body wash B most of the carrier and fragrance are solubilized by the surfactant micelles.

Example 3

Figure 3:
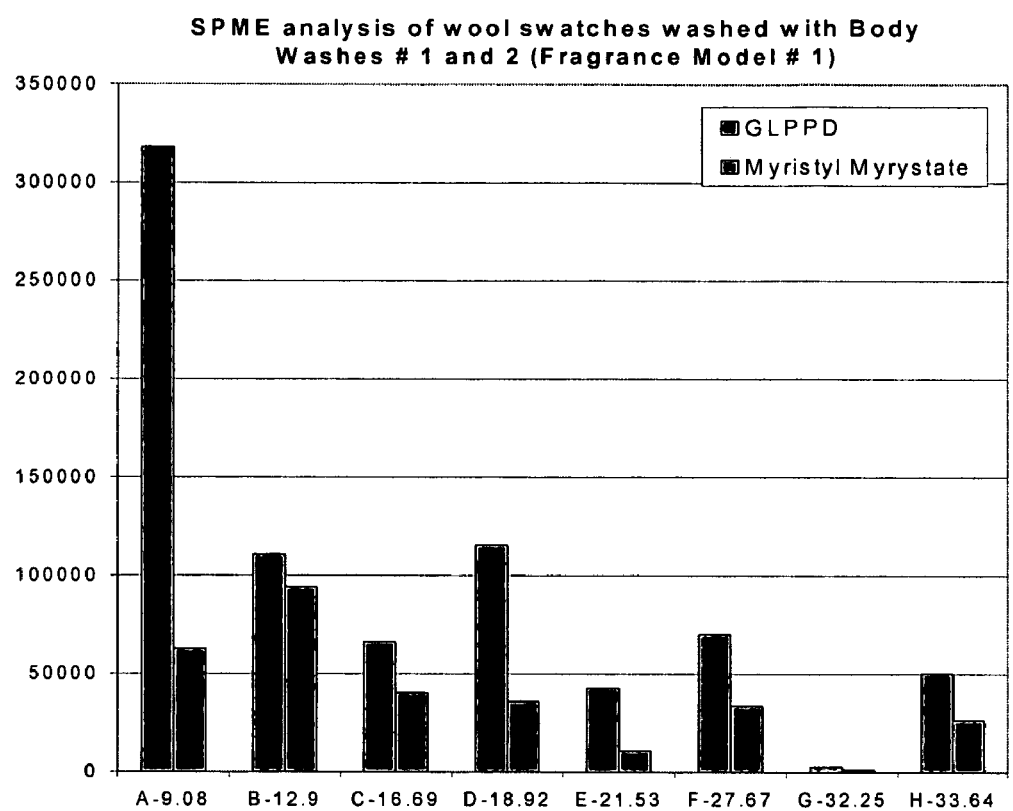
FIG. 3 shows the results of a comparative analysis of fragrance deposition attained with prior art delivery systems, against that obtained with the GLPPD according to the present invention, as described in Example 3.

Application of Body Washes to Wool Surfaces and Measure of Fragrance Deposition on the Surface Treated A comparative analysis of fragrance deposition attained with prior art delivery systems, against the GLPPD object of the present invention, is illustrated in FIG. 3. This Figure represents a typical chromatographic analysis of a fragrance deposited on wool after washing with two body washes, namely, one containing myristyl myristate and the other polymer isomyristyl alcohol dimer/IPDI as the fragrance carrier. In the "Y" axis of this graph are represented the area count units associated with each raw material intensity, while in the "X" axis are represented the raw material chromatographic peaks by retention time. The invention body wash composition used in this experiment was previously already described in Example 1. Fragrance raw material analysis was carried out by SPME in the head space of vials containing the wool swatch. The composition of the model and their associated retention times (RT) were as follows: Limonene (RT=9.08); Benzyl Acetate (RT=12.9); Cyclohexane ethanol, Acetate (RT=16.69); Cyclohexanol, 2-(1,1-dimethylethyl)-, acetate (RT=18.92); Undecanal, 2-methyl (RT=21.53); Benzenepropanal, 4-(1,1-dimethylethyl)-alpha methyl (RT=27.67); Cyclopentaneacetic acid, 3-oxo-2-pentyl-, methylester (RT=32.25); Hexyl Salicylate (RT=33.64).

An analysis of FIG. 3 reveals, overall, that the level of fragrance deposition obtained using the GLPPD as fragrance carrier, and object of the present invention, is higher than that attained using a common fatty ester as the fragrance carrier.

Example 4

Preparation of Body Wash Compositions According to the Invention

Two body wash compositions were prepared by admixing, as described below, the following ingredients in the proportions indicated:
1) Fragrance # 2: 1.0 g of fragrance containing the following raw materials: Limonene (RT 9.45); Dihydromercenol (RT 10.46); Phenylethyl alcohol (RT 11.43); Cyclohexane ethanol Acetate (RT 16.91); Verdox (RT 19.10); Veloutone (RT 19.78); Lillial (RT 27.97); Amyl Salicylate (RT 28.46 and 29.31); Hexyl Salicylate (RT: 33.77); Galaxolide (RT: 39.91).
2) Mixture of polymers for external dispersing, respectively internal dispersible phases: 0.1 g of Acrylamidopropyltrimonium Chloride (and) Acrylamide copolymer (SALCARE® SC-60); 1.0 g Trimethylaminoethyl Methacrylate Chloride (SALCARE® SC-96)
3) Primary Surfactant 1: 15.0 g of Sodium Laureth-2 Sulfate
4) Secondary Surfactants: 3.0 g of Cocamido Propyl Betaine
5) Internal phase stabilizer: 2.0 g Trihydroxystearine
6) Internal phase stabilizer: 0.5 g Sorbitan Iso-stearate
7) Stabilizer/thickener: 1.0 g Pentaerythrityl Tetrastearate (and) PEG-6 Caprylic/Capric Glycerides (and) Water
8) Preservative: 0.1 g DMDM Hydantoin
9) Water: To complete 100 g Part A: The Acrylamidopropyltrimonium Chloride (and) Acrylamide copolymer cationic dispersing polymer (delivery polymer 1) was hydrated by gradually mixing 0.5 g of polymer in 20 g of water until a clear solution was obtained. Then, polymer Trimethylaminoethyl Methacrylate Chloride (SALCARE® SC-96; carrier polymer 2) and the fragrance were added to hydrated polymer 1 to form an opaque mixture. Part B: The primary, secondary, and stabilizing surfactants, and thickeners were mixed and heated to 70° C. The remaining water was added as needed.

Part A was admixed with part B at 40 C, the mixture was, then, thoroughly stirred to form the surfactant/polymer complex or GLPPD, object of the invention. After thorough mixing the body wash composition was cooled to room temperature.

Figure 4:
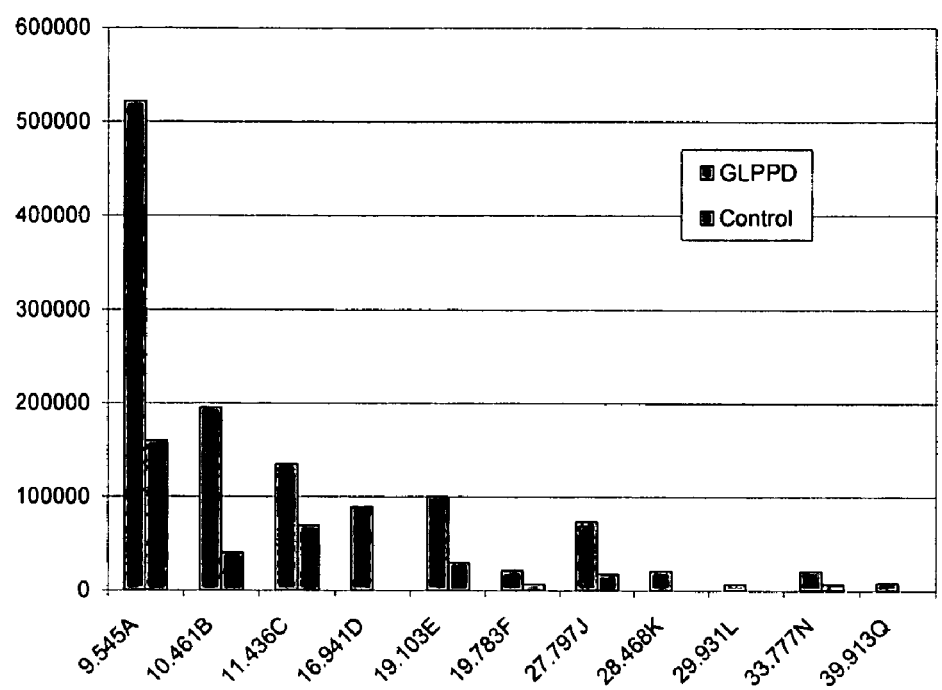
FIG. 4 shows the results of a comparative analysis of fragrance deposition attained with prior art Control delivery systems, against that obtained with the GLPPD according to the present invention, as described in Example 4.

An analysis of FIG. 4 reveals, overall, that the level of fragrance deposition obtained using the GLPPD as fragrance carrier, and object of the present invention, is higher than that attained using the same body wash formulation but without the polymer gel complex, or CONTROL.

Example 5

Preparation of a Shampoo Composition According to the Invention

A shampoo composition was prepared by admixing, as described below, the following ingredients in the proportions indicated:
1) Fragrance # 3: 1.0 g of fragrance containing the following raw materials: Dihydromercenol (RT 10.56); Linalol (RT 11.49); Terpinyl Acetate (RT 21.07); Jasmal (RT 25.94); Lilial (RT: 27.73); Verdyl Propionate (RT 28.20); Undecalactone (RT 29.33); Hexyl Salicylate (RT 33.70); Iso-E Super (RT 34.52); Habanolide (RT 39.59); Galaxolide (RT 40.04).
2) Polymers for external dispersing phase, respectively internal dispersing phase: 0.1 g of Acrylamidopropyltrimonium Chloride (and) Acrylamide copolymer (SALCARE® SC-60); 1.0 g Polyvinylamine (LUPAMIN® 9096)
3) Primary Surfactant 1: 15.0 g of Sodium Laureth-2 Sulfate
4) Secondary Surfactants: 3.0 g of Cocamido Propyl Betaine
5) Internal phase stabilizer: 2.0 g Trihydroxystearine
6) Internal phase stabilizer: 0.5 g Sorbitan Iso-stearate
7) Stabilizer/thickener: 1.0 g Pentaerythrityl Tetrastearate (and) PEG-6 Caprylic/Capric Glycerides (and) Water
8) Preservative: 0.1 g DMDM Hydantoin
9) Water: To complete 100 g Part A: The Acrylamidopropyltrimonium Chloride (and) Acrylamide copolymer cationic dispersing polymer (delivery polymer 1) was hydrated by gradually mixing 0.5 g of polymer in 20 g of water until a clear solution was obtained. Then, polymer Polyvinylamine (carrier polymer 2) and the fragrance were added to polymer 1 to form a mixture. Part B: The primary, secondary, and stabilizing surfactants, and thickeners were mixed and heated to 70 C. The remaining water was added as needed.

Part A was admixed with part B at 40 C, the mixture was, then, thoroughly stirred to form the surfactant/polymer gel complex or GLPPD, object of the invention. After thorough mixing the shampoo composition was cooled to room temperature.

Figure 5:
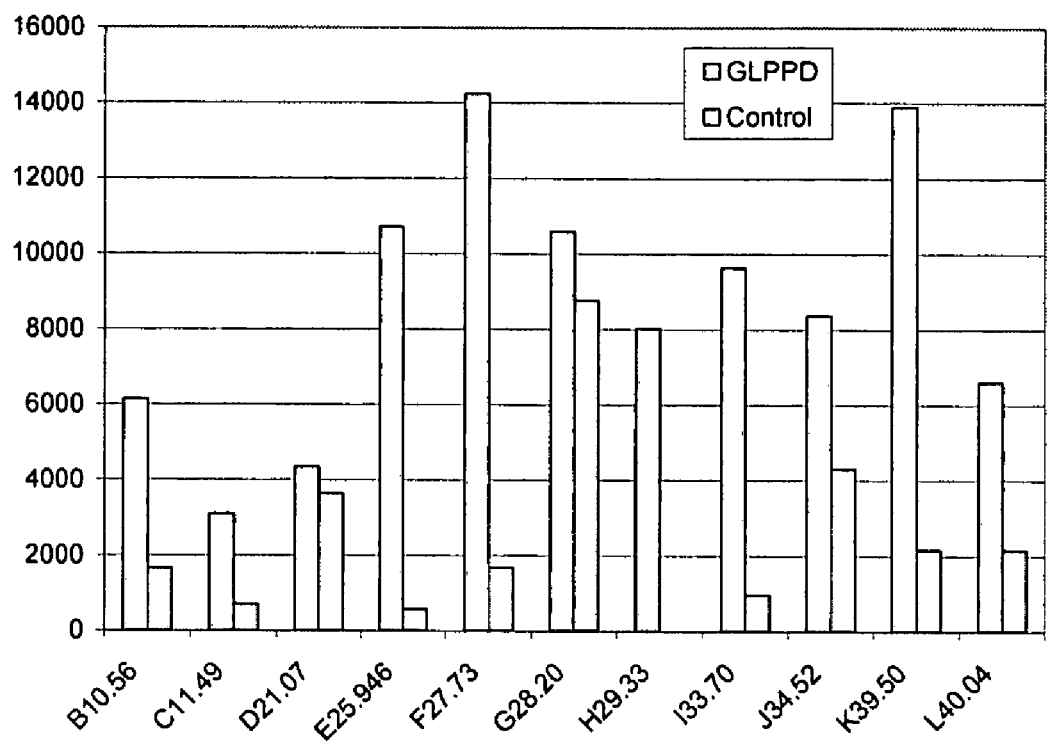
FIG. 5 shows the results of a comparative analysis of fragrance deposition attained with prior art Control delivery systems, against that obtained with the GLPPD according to the present invention, as described in Example 5.

An analysis of FIG. 5 reveals, overall, that the level of fragrance deposition obtained using the GLPPD as fragrance carrier, and object of the present invention, is higher than that attained using the same shampoo formulation but without the polymer gel complex, or CONTROL.

What is claimed is:

1. A carrier and delivery system for a hydrophobic benefit agent, comprising: a) a water miscible cationic polymer or mixture of polymers susceptible of forming a gel able to complex a surfactant system; b) one or more water immiscible liquid polymers or oligomers susceptible of complexing said surfactant system; and c) a hydrophobic benefit agent; wherein said cationic polymer or mixture of polymers comprises an acrylamide polymer.

2. A carrier system according to claim 1, wherein the hydrophobic benefit agent is a fragrance.

3. A carrier system according to claim 1, capable of forming a gel-liquid polymer/polymer dispersion (GLPPD) with a surface cleansing surfactant.

4. A carrier system according to claim 1, wherein the water miscible cationic polymer or mixture of polymers has a high degree of cationic substitution, a molecular weight higher than 400 K and a cationic charge ranging from 1 to 30 meq/g.

5. A carrier system according to claim 4, wherein the water miscible cationic polymer or mixture of polymers is selected from the group consisting of polyethylenimine PS, cationic polyamine, cationic polyacrylamide, trimethylaminoethyl methacrylate chloride polymer, polyvinylamine, polydimethyldiallyl Ammonium Chloride, polyquaternium-10, and their mixtures.

6. A carrier system according to claim 1, wherein the water immiscible liquid polymers or oligomers able to complex with the surfactant base have a viscosity comprised between 500 and 20,000 cps.

7. A method for the preparation of a carrier system according to claim 1, which comprises: a) mixing the water immiscible liquid polymers or oligomers with the benefit hydrophobic ingredient to obtain a water dispersible phase; b) hydrating the water miscible cationic polymer or mixture of cationic polymers in a water-containing medium so as to obtain an aqueous polymer solution able to form a dispersing phase; and c) mixing the dispersible and dispersing phases to form the carrier system of the hydrophobic agent.

8. A gel-liquid polymer/polymer dispersion (GLPPD) comprising a surfactant, susceptible of being obtained by admixing: a) a dispersing phase which is a cationic polymer or mixture of polymers susceptible of complexing said surfactant to form an aqueous gel; b) a dispersible phase formed of at least a water immiscible liquid polymer or oligomer, or a mixture thereof, capable of forming a liquid complex with said surfactant; and c) a hydrophobic active agent, wherein said cationic polymer or mixture of polymers comprises an acrylamide polymer.

9. A GLPPD according to claim 8, which further comprises a stabilizer of the dispersible phase.

10. A gel-liquid polymer/polymer dispersion (GLPPD) comprising a surfactant, susceptible of being obtained by admixing: a) a dispersing phase which is a cationic polymer or mixture of polymers susceptible of complexing said surfactant to form an aqueous gel; b) a dispersible phase formed of at least a water immiscible liquid polymer or oligomer, or a mixture thereof, capable of forming a liquid complex with said surfactant; c) a hydrophobic active agent; and d) a stabilizer selected from trihydroxystearin, polysorbate 20, sorbitan isostearate and mixtures thereof.

11. A GLPPD according to claim 10, wherein the water miscible cationic polymer or mixture of polymers has a high degree of cationic substitution, a molecular weight higher than 400 K and a cationic charge ranging from 1 to 30 meq/g.

12. A GLPPD according to claim 11, wherein the water miscible cationic polymer or mixture of polymers is selected from the group consisting of polyethylenimine PS, cationic polyamine, cationic polyacrylamide, trimethylaminoethyl methacrylate chloride polymer, polyvinylamine, polydimethyldiallyl Ammonium Chloride, polyquaternium-10, their mixtures, and mixtures thereof with an acrylamide polymer.

13. A GLPPD according to claim 8, wherein the water immiscible liquid polymers or oligomers able to complex with the surfactant base have a viscosity comprised between 500 and 20,000 cps.

14. A method for the preparation of a GLPPD according to claim 8, which comprises: a) mixing the water immiscible dispersible polymers or oligomers with the benefit of a hydrophobic ingredient to obtain a water dispersible phase; b) hydrating the cationic polymer or mixture of cationic polymers in a water-containing medium so as to obtain an aqueous polymer solution forming a dispersing phase; c) mixing the dispersible and dispersing phases to form a pre-mix carrier system of the hydrophobic agent; and d) combining the pre-mix carrier system with a surfactant system and optionally a stabiliser of the dispersible phase, in appropriate relative proportions, so as to obtain a surfactant complex gel.

15. A perfumed consumer product, comprising a micelle forming surfactant and a fragrance, wherein the fragrance is in the form of a carrier system according to claim 1.

16. A perfumed consumer product according to claim 15, in the form of a cleaning or conditioner composition for treating the skin, hair, textiles or other surfaces.

17. A perfumed consumer product according to claim 16, which is a bath or shower wash, a soap, a detergent or fabric softener, a dish or window cleaner, or a heavy duty cleaner.

18. A perfumed consumer product, comprising a micelle forming surfactant, water and a GLPPD according to claim 8.

19. A perfumed consumer product according to claim 18, in the form of a cleaning or conditioner composition for treating the skin, hair, textiles or other surfaces.

20. A perfumed consumer product according to claim 19, which is a bath or shower wash, a soap, a detergent or fabric softener, a dish or window cleaner, or a heavy duty cleaner.

21. A method for the preparation of a GLPPD according to claim 10, which comprises: a) mixing the water immiscible dispersible polymers or oligomers with the benefit of a hydrophobic ingredient to obtain a water dispersible phase; b) hydrating the cationic polymer or mixture of cationic polymers in a water-containing medium so as to obtain an aqueous polymer solution forming a dispersing phase; c) mixing the dispersible and dispersing phases to form a pre-mix carrier system of the hydrophobic agent; and d) combining the pre-mix carrier system with a surfactant system and the stabiliser of the dispersible phase, in appropriate relative proportions, so as to obtain a surfactant complex gel.

22. A carrier system according to claim 1, wherein the water immiscible liquid polymers or oligomers are selected from the group consisting of polymers and oligomers derived from isophorone di-isocyanate, hydrogenated polyisobutene/polybutene copolymers, hydrogenated polydecene and mixtures thereof.

23. A carrier system according to claim 1, wherein the acrylamide polymer is an acrylamidopropyltrimonium chloride acrylamide copolymer.

24. A carrier system according to claim 8, wherein the acrylamide polymer is an acrylamidopropyltrimonium chloride acrylamide copolymer.

25. A carrier system according to claim 8, wherein the water immiscible liquid polymers or oligomers are selected from the group consisting of polymers and oligomers derived from isophorone di-isocyanate, hydrogenated polyisobutene/polybutene copolymers, hydrogenated polydecene and mixtures thereof.

26. A carrier system according to claim 8, wherein the hydrophobic benefit agent is a fragrance.

27. A carrier system according to claim 8, wherein the water miscible cationic polymer or mixture of polymers has a high degree of cationic substitution, a molecular weight higher than 400 K and a cationic charge ranging from 1 to 30 meq/g.

28. A carrier system according to claim 8, wherein the water miscible cationic polymer or mixture of polymers is selected from the group consisting of polyethylenimine, cationic polyamine, cationic polyacrylamide, trimethylaminoethyl methacrylate chloride polymer, polyvinylamine, polydimethyldiallyl Ammonium Chloride, polyquaternium-10 and their mixtures.

29. A carrier system according to claim 8, wherein the water immiscible liquid polymers or oligomers able to complex with the surfactant base have a viscosity comprised between 500 and 20,000 cps.

30. A carrier system according to claim 12, wherein the acrylamide polymer is an acrylamidopropyltrimonium chloride acrylamide copolymer or trimethylaminoethyl methacrylate chloride polymer.

31. A GLPPD according to claim 10, wherein said cationic polymer or mixture of polymers comprises an acrylamide polymer.

32. A carrier system according to claim 10, wherein the water immiscible liquid polymers or oligomers are selected from the group consisting of polymers and oligomers derived from isophorone di-isocyanate, hydrogenated polyisobutene/polybutene copolymers, hydrogenated polydecene and mixtures thereof.

33. A GLPPD according to claim 10, wherein the water immiscible liquid polymers or oligomers able to complex with the surfactant base have a viscosity comprised between 500 and 20,000 cps.

34. A perfumed consumer product, comprising a micelle forming surfactant, water and a GLPPD according to claim 10.

35. A perfumed consumer product according to claim 34, in the form of a cleaning or conditioner composition for treating the skin, hair, textiles or other surfaces.

36. A perfumed consumer product according to claim 35, which is a bath or shower wash, a soap, a detergent or fabric softener, a dish or window cleaner, or a heavy duty cleaner.

* * * * *